United States Patent [19]
Venkataramani et al.

[11] Patent Number: 5,449,819
[45] Date of Patent: Sep. 12, 1995

[54] PROCESS FOR REMOVING WASTE POX, ALENDRONATE AND ITS BY PRODUCTS

[75] Inventors: Edamanal S. Venkataramani, Berkeley Heights; Andrew L. Forman, Rahway; Ralph J. Magliette, Jr., Piscataway; Donald McKinney, Freehold, all of N.J.

[73] Assignee: Merck & Co., Inc., Rahway, N.J.

[21] Appl. No.: 254,805

[22] Filed: Jun. 6, 1994

[51] Int. Cl.$^6$ .............................................. C07F 9/38
[52] U.S. Cl. ................................... 562/13; 210/724; 210/906; 423/321.1; 562/8; 562/124
[58] Field of Search .......................... 562/8, 13, 124; 423/321.1; 210/724, 906

[56] References Cited

U.S. PATENT DOCUMENTS

| | | | |
|---|---|---|---|
| 3,716,484 | 2/1973 | Lincoln et al. | 210/52 |
| 3,816,306 | 6/1974 | Roy | 210/49 |
| 4,250,107 | 2/1981 | Sommer et al. | 260/502.5 |
| 4,308,147 | 12/1981 | Sommer et al. | 210/700 |
| 4,450,047 | 5/1984 | Malzahn | 203/15 |
| 4,689,154 | 8/1987 | Zimberg | 210/667 |
| 4,922,007 | 5/1990 | Kieczykowski et al. | 562/13 |
| 4,938,846 | 7/1990 | Comstock et al. | 203/15 |
| 5,019,651 | 5/1991 | Kieczykowski | 562/13 |

OTHER PUBLICATIONS

M. Afzal and J. Ahmed "Harned/Akerlof Equations and the solubility of NaCl in HCl–water system", Pakistan *J. Sci. Ind. Res.*, vol. 17, No. 6, 1974.

S. C. Baker and J. C. Jurrell, "Microbial Degradation of Methanesulphonic acid: A Missing Link in the Biogeochemical Sulfer Cycle", *Nature,* 350:527–8, 1991.

E. Miller "Vapor–Liquid Equilibria below 0° C. of hydrogen chloride solutions saturated with calcium chloride", *J. Chem. Eng. Data,* vol. 35, No. 4: 436–440, 1990.

R. W. Potter III, and M. A. Clynne, *J. Chem. Eng. Data,* vol. 25: 50–51, 1980.

J. Ruth, "Odor Thresholds and Irritation Levels of Several Chemical Substances: A Review", *Am. Ind. Hyg. Assoc. J.,* 47:141–150, 1986.

T. Sako et al., "Salt effects of vapor–liquid equilibria for volatile strong electrolyte–water systems", *J. Chem. Eng. Jap* (English), vol. 17, No. 4, 381–388, 1984.

E. S. Venkataramani et al., "Create Drugs, Not Waste—Case Histories of One Company's Successes", *Chemtech,* p. 674, Nov. 1992.

D. E. Wierenga and C. R. Eaton "The Drug Development and Approval Process", p. 10 in *New Drug Approvals in 1992* presented by the Pharm. Mfgs. Assoc., Jan. 1992.

*Primary Examiner*—José G. Dees
*Assistant Examiner*—Barbara S. Frazier
*Attorney, Agent, or Firm*—Robert J. North; Melvin Winokur; Joseph F. DiPrima

[57] ABSTRACT

Disclosed is a process for removing by-product phosphorus-containing ($PO_x$) materials, alendronate and alendronate byproducts from crude mother liquors in an omega amino-1-hydroxy-$C_2$–$C_6$ alkylidene-1,1-bis-phosphonic acid synthesis process, e.g. alendronate sodium. Calcium chloride is added first to the crude mother liquors, then calcium oxide to precipitate the $PO_x$ materials, then neutralized to about pH 7 to complete precipitation. Substantially all of the alendronate sodium active ingredient is removed from the precipitate. Following filtration, the $PO_x$ filtercake can then be disposed of by incineration, landfilling or reclamation of usable phosphorus as fertilizer. The remaining filtrate can then be further treated in an environmentally acceptable manner by wastewater treatment or recycling to the process.

10 Claims, 3 Drawing Sheets

STEP 1:

γ-AMINOBUTYRIC ACID
MW 103.1

PYROPHOSPHONATE
MW 295

+ HCl(g) + OLIGOMERS

STEP 2:

PYROPHOSPHONATE
MW 295

SODIUM PYROPHOSPHONATE
MW 295

STEP 3:

SODIUM PYROPHOSPHONATE
MW 295

ALENDRONATE SODIUM
TRIHYDRATE
MW 325.1

PROCESS FOR REMOVING WASTE POX, ALENDRONATE AND ITS BY PRODUCTS

BACKGROUND OF THE INVENTION

1. Field of the Invention

This invention relates to a process for removing phosphorus-containing materials, POx, alendronate and alendronate byproducts from crude process mother liquors in a bisphosphonate synthesis using a $CaCl_2$/CaO precipitation/neutralization and filtration procedure.

2. Brief Description of Disclosures in the Art

Alendronate sodium, 4-amino-1-hydroxybutylidene-1-bisphosphonic acid monosodium trihydrate, is a promising new agent for combatting bone resorption in bone diseases including osteoporosis, particularly in post-menopausal women. The compound, utility and method of preparation are described in U.S. Pat. Nos. 4,922,007 and 5,019,651, both assigned to Merck & Co., Inc.

Large scale processes as described in the above patents for producing alendronate sodium generate large volumes of soluble phosphorus-containing materials ($PO_x$) including sodium salts of phosphates, phosphites and pyrophosphates as waste.

Generally, wastewater treatment processing (WWTP) facilities can handle on a total daily basis of about 1–10 ppm (mg/L) of phosphorus per liter of waste.

However, the alendronate process can generate as much as 500 mg of phosphorus as $PO_x$ per liter of waste per day greatly exceeding the allowable limit in many geographic regions for wastewater processing and discharge of effluent.

One general method for dealing with this problem has involved passing the wastestream to an acclimated sludge culture to biodegrade the waste $PO_x$ and methanesulfonic acid (MSA) materials.

However, this method suffers from the low amount of $PO_x$/MSA that an activated sludge can process on a daily basis. For example, out of a waste load of 1000 lbs., of biological oxygen demand (BOD) material, the sludge can, generally only handle 5–10 lbs./day of phosphorus as a bacterial food supplement.

What is desired in the art is a process for recovering and non-process reuse of wastewater phosphorus-containing materials, $PO_x$, in an environmentally safe, efficient and cost-effective manner.

SUMMARY OF THE INVENTION

We have found that the residual phosphorus-containing materials, $PO_x$, in aqueous crude mother liquors from the alendronate sodium bisphosphonate process can be efficiently removed by a precipitation method involving the addition of calcium chloride, then the addition of lime, followed by neutralization and filtration. The crude $PO_x$ containing filtercake, which also contains residual waste alendronate and alendronate byproducts, can be disposed of by environmentally acceptable methods, e.g. landfilling, incineration or reclamation of phosphorus as fertilizer.

By this invention there is provided a process comprising the steps of:

a) contacting an aqueous medium, of about pH of 4–8, e.g., solution, comprised of salts, e.g., sodium, potassium, calcium, of omega amino $C_2$–$C_6$ alkylidene-1-hydroxy-1,1-bisphosphonic acid, methanesulfonic acid, phosphorous acid and phosphoric acid, with calcium chloride compound in an amount of 2–10 parts by weight of calcium chloride, taken as the anhydrous salt, to 100 parts by volume of the medium, at about room temperature;

b) contacting said medium from step (a) with calcium oxide in a sufficient amount to increase the pH to about 10–12 to cause precipitation of calcium/phosphorus containing salts;

c) contacting said mixture from step (b) with acid e.g., hydrochloric acid, sulfuric acid, to adjust the pH of the aqueous portion of the mixture to about 6–8 to cause substantially complete precipitation of calcium/phosphorus containing salts;

d) separating said precipitated mixture of calcium/phosphorus containing salts from the aqueous medium.

BRIEF DESCRIPTION OF THE INVENTION AND PREFERRED EMBODIMENT

Figure 1:
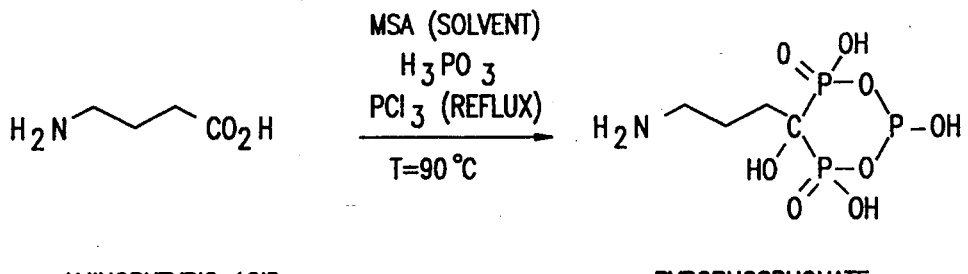
FIG. 1 illustrates the overall chemistry of the bisphosphonate process for producing alendronate sodium.
Figure 1:
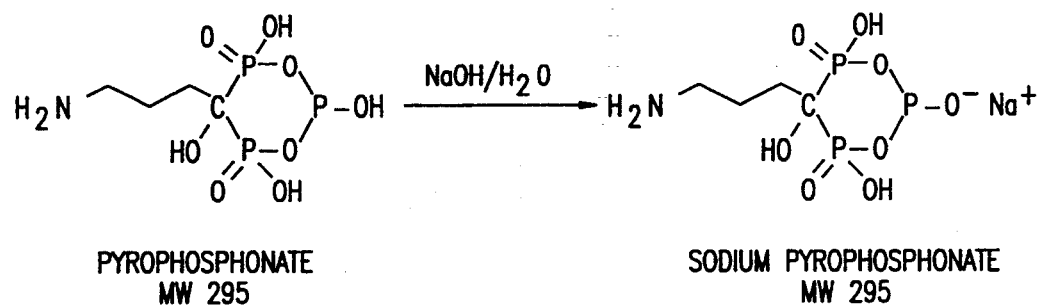
Figure 1:
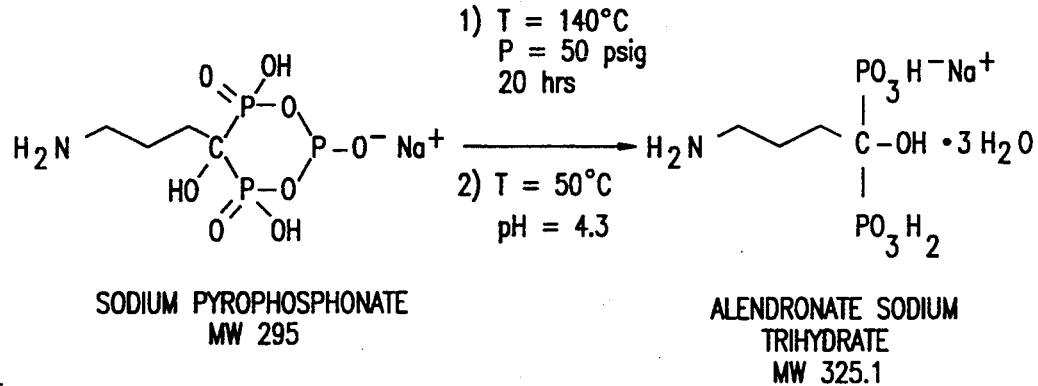

The overall alendronate sodium process chemistry as shown in FIG. 1 includes three steps: a bisphosphonation reaction, a pH controlled aqueous quench and a hydrolysis/crude crystallization step. The process can be carried out either as a batch or continuous process utilizing standard apparatus.

In the bisphosphonation reaction, (see U.S. Pat. No. 4,922,007) gamma-aminobutyric acid (GABA) is reacted with phosphorus trichloride ($PCl_3$) and phosphorous acid ($H_3PO_3$) in methanesulfonic acid (MSA) as solvent under reflux temperature, e.g. 80°–100° C. for about 0.5 to 3 hours. The reaction can generally be carded out at atmospheric pressure. As seen in FIG. 1, the initial product in the reaction is pyrophosphate (PP) and multimeric alendronate precursors (not shown).

The reaction mixture is then quenched into water under pH control using aqueous caustic at a maintained pH of about 4 to 7. Then the pH is adjusted to 4–5, e.g., 4.3–4.7 and heated under pressure, e.g. 1 to 10 atmospheres, a useful range being 1–4 atmospheres, at a temperature of about 100° to 150° C. for about 2 to 30 hours to substantially convert the pyrophosphate and multimeric precursors to alendronate sodium. The small residual fraction which is not converted to alendronate sodium is termed "alendronate byproducts".

The crude crystallization is carded out by cooling the hydrolysis mixture to about 10°–60° C., e.g., 50° C. and adjusting the pH to about 4–5, a useful range being 4.2–4.7, by the addition of aqueous caustic or hydrochloric acid, producing crystalline alendronate sodium (trihydrated) which is filtered, collected, purified and processed.

Figure 2:
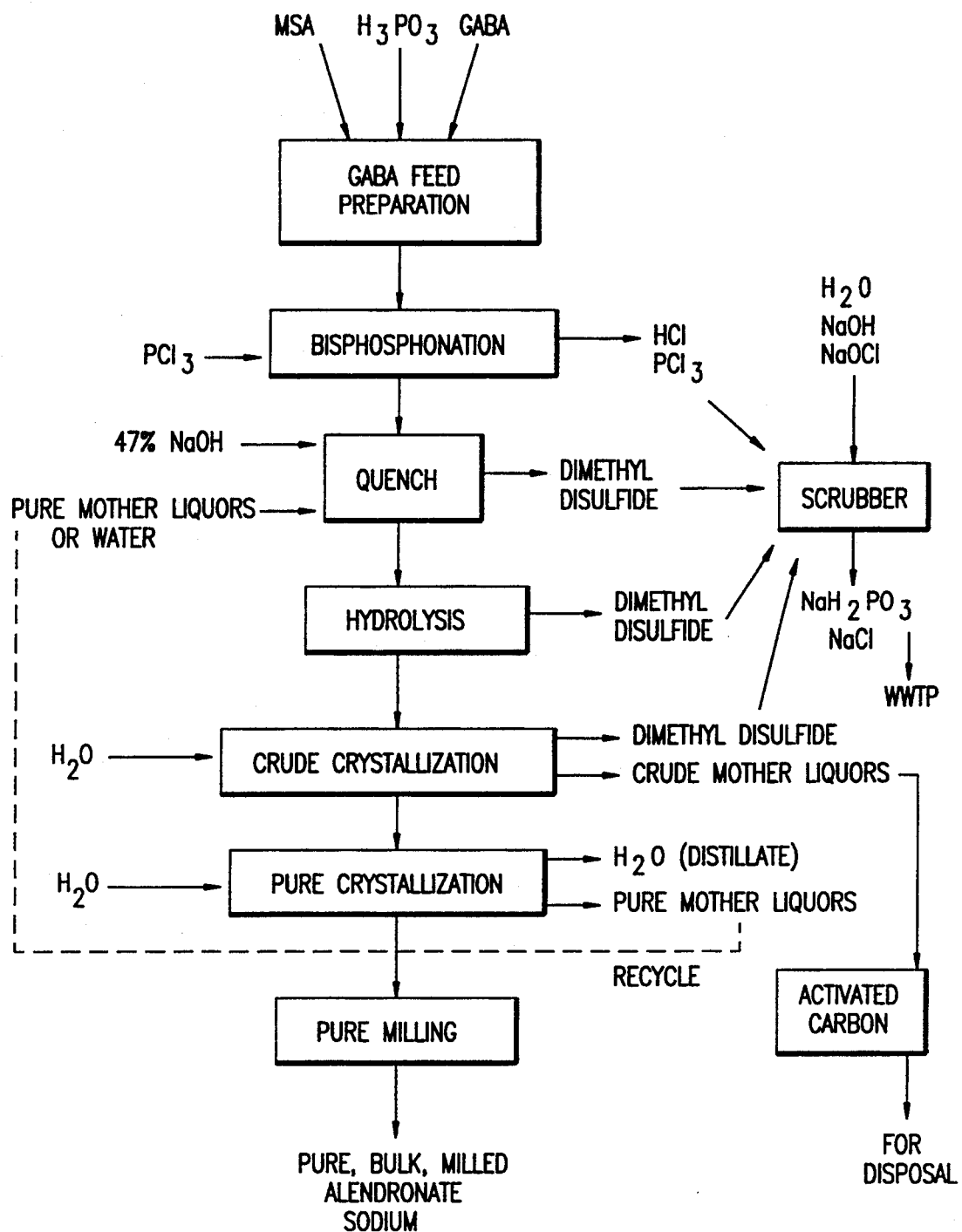
FIG. 2 illustrates the overall bisphosphonate process flowsheet for alendronate sodium manufacture.

The overall process flowsheet for alendronate sodium manufacture is shown in FIG. 2.

As seen, GABA feed is prepared from a mixture of GABA, MSA and $H_3PO_3$ and fed into the bisphosphonation reaction vessel together with $PCl_3$ to form the pyrophosphate (PP).

After the bisphosphonation step, the reaction mixture is reacted with aqueous caustic in a quench step under controlled pH conditions of pH 4 to 7 to form sodium pyrophosphate (other pyrophosphates not shown) and then heated under elevated pressure and temperature in a subsequent hydrolysis step to form alendronate sodium.

The hydrolysis mixture is cooled, the pH is adjusted to 4 to 5 and alendronate monosodium trihydrate is allowed to precipitate as a crude crystallization mass.

The crude crystallized alendronate sodium is filtered, the wet cake washed with a minimum of cold demineralized (DM) water, separated from the crude mother liquors and then subjected to a pure crystallization step from water.

The pure crystallized alendronate sodium being of pharmaceutically acceptable quality, is collected, and milled to produce pure, bulk, milled alendronate sodium, which can be further processed for pharmaceutical dosage formulation.

The gaseous side products from the bisphosphonation step, consisting mainly of HCl, $PCl_3$ and vapor from the quench and crude steps containing trace amounts of dimethyldisulfide (DMDS), are passed to a scrubber containing water, caustic and sodium hypochlorite to produce a wastewater process stream containing predominantly a mixture of $Na_2HPO_3$, $Na_2HPO_4$, $Na_3PO_3$, $Na_3PO_4$, and sodium chloride which can be discharged to a wastewater facility under controlled conditions. The crude mother liquors (MLs) can be passed over a bed of activated carbon to remove dimethyldisulfide, DMDS, and the filtrate collected in a tank for $PO_x$/alendronate precipitation. $PO_x$ may be partially or totally removed by the $CaCl_2$/CaO precipitation procedure described herein.

Figure 3:
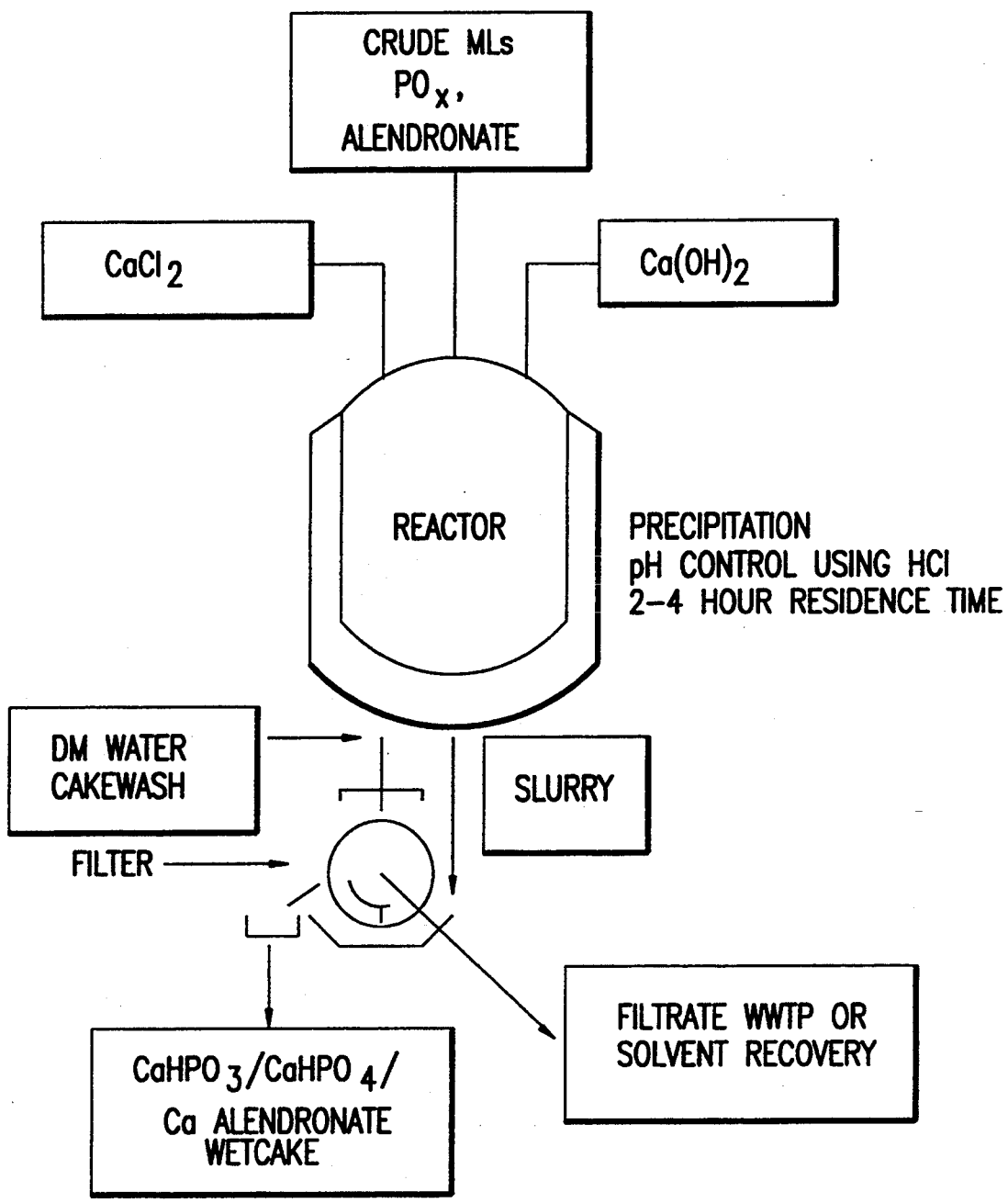
FIG. 3 illustrates the calcium precipitation/phosphorus removal step.

The crude mother liquors are first passed over a bed of activated carbon to remove dimethyldisulfide (DMDS) and are then passed to a precipitation tank for $CaCl_2$/lime/pH adjustment as shown in FIG. 3.

The novel aspect of this invention involves a new way for treatment/reuse/disposal of the crude mother liquors produced.

The crude mother liquors (MLs) contain about 5–10% by weight phosphate and phosphite as $PO_x$, 22–25% MSA, 5% NaCl, 1–2% GABA, 0.5–1% alendronate sodium and byproducts and 60–65% water.

In the initial step, $CaCl_2$ compound is added in an amount of about 2 to 10 weight percent by volume of mother liquor, and usually 2–4 w/v percent, taken as anhydrous $CaCl_2$. The $CaCl_2$ is generally used for convenience as the hexahydrate, although the anhydrous form, being expensive, can also be used. The purpose of adding $CaCl_2$ first in the process is to increase the ionic strength of the liquid medium and to salt out subsequently formed calcium/phosphorus salts.

Next, CaO (lime) is added in sufficient quantity usually 3–7 weight by volume percent, and usually about 5 w/v %, to dissolve in the mother liquors and to produce a pH of about 10–12 to facilitate subsequent precipitation of the $PO_x$ species.

Next, the mixture is neutralized by the addition of e.g. hydrochloric acid to lower the pH to about 6–8, e.g, 7. The resulting slurry is stirred for about 2–4 hours to insure maximum possible precipitation of all the $PO_x$ species in the mother liquors.

Eliminating the $CaCl_2$ addition or the neutralization step, all result in lowered $PO_x$ recovery. $PO_x$ recoveries of about 90–95+% are achieved by this disclosed invention method. However, using the CaO step alone gives about 60% recovery. Furthermore, using $CaCl_2$/CaO addition without the neutralization step results in about 88% recovery.

An additional advantage of this $PO_x$ removal methodology is that residual alendronate sodium, being the active drug ingredient, as well as alendronate byproducts, are also selectively and quantitatively removed from the $PO_x$ filtercake.

After the CaO precipitation, the slurry is filtered and washed with water, a useful form being demineralized (DM) water. The filtrates are cycled to the wastewater treatment plant, or to solvent recovery, or if sufficiently low in $PO_x$, to a separate bacterial biodegradation step for MSA treatment prior to passing to WWTP.

A microbial biodegradation step can be used involving an acclimated sludge culture for biodegrading MSA, in which increasing concentrations of MSA, in wastewater are fed to the sludge while maintaining the pH, BOD, hydraulic residence time and sludge density within optimized process limits.

The precipitated $PO_x$ filtercake, which contains predominantly $CaHPO_3$, $CaHPO_4$ and calcium alendronate, can be dried and used on landfill, incinerated or recycled to a fertilizer plant for extraction of usable phosphorus.

At moderate production levels, this process can be carded out in batch mode. However, the $PO_x$ reduction process is also amenable to continuous operation at full production scale.

The $PO_x$ removal efficiencies in the process are a function of the reagents used and the pH. An alternative reagent useful in the precipitation of $PO_x$ is $Al(OH)_3$, but this only adds a new cation to an already complex waste stream. Also, $Al^{+++}$ was found to be less effective than $Ca^{++}$ in the removal of $PO_x$ from this stream.

The described $PO_x$ recovery process can also be used in other bisphosphonation processes where the appropriate amino acid starting material can be used to produce the following omega amino $C_2$–$C_6$ alkylidene-1,1-bisphosphonic acids: 2-amino-1-hydroxy-isobutylidene-1,1-bisphosphonic acid, 3-amino-1-hydroxy-propylidene-1,1-bisphosphonic acid, 5-amino-1-hydroxypentylidene-1,1-bisphosphonic acid and 6-amino-1-hydroxyhexylidene-1,1-bisphosphonic acid. The term "omega amino" is used herein to indicate the presence of an amino group on the terminal carbon of the alkylidene chain at the other end from the bisphosphonate carbon atom.

The following examples are illustrative of carrying out the invention as contemplated by the inventors.

EXAMPLE 1

$CaCl_2$/CaO/Neutralization

To 1 liter of carbon treated (to remove DMDS) alendronate sodium Crude MLs (pH ~4.5) at room temperature (20°–25° C.), is added 70 g of calcium chloride ($CaCl_2$) and stirred for 15 minutes (pH ~4, T=20°–25° C.).

Next, 50 g of lime (CaO) is added, and mixed rapidly for 30 minutes (pH 12). The pH and temperature generally increase to about 12 and ~45° C., respectively.

Next, concentrated HCl (36%) is added to adjust the pH of the mixture to about 7. Several additions of HCl may be required to stabilize the pH to 7. Approximately 75 mL of 36% HCl is required. Neutralization is complete when the pH is stabilized at about 7 for at least 10 minutes. The temperature rise is usually minimal ($\leq 5°$ C.).

The mixture is allowed to stir for 5 minutes, then filtered using a Whatman #4 filter paper in a Buchner Funnel using vacuum. The filtercake is washed with 2–5 volumes of DM water to remove residual MSA from the NaCl filter cake. The washings are combined with the filtrate for MSA recovery. The total time for filtration is generally about $\leq 1$ hr.

The filtrate can be treated by an activated sludge system, described above. The $CaPO_x$ cake is saved for ultimate disposal.

The $PO_x$ removal efficiency is 96–98%.

The overall process for the removal of $PO_x$ can be written as:

Crude MLs +70 g/L $CaCl_2$ (mixing) +50 g/L lime (mixing) +pH adjustment using HCl to ~7, followed by filtration and DM water wash.

Repeating the above process in the absence of the $CaCl_2$ addition and neutralization steps only results in a $PO_x$ recovery of about Repeating the above process in the absence of the final pH neutralization step only results in a $PO_x$ recovery of about 88%. 60%.

References

Baker, S. C., Kelly, D. P., and Murrell, J. C., "Microbial Degradation of Methanesulphonic acid: A Missing Link in the Biogeochemical Sulfur Cycle", *Nature*, 350:527–8, 1991.

Ruth, J., "Odor Thresholds and Irritation Levels of Several Chemical Substances: A Review", *Am. Ind. Hyg. Assoc. J.*, 47, 142–150, 1986.

U.S. Pat. No. 4,938,846 to Comstock, et al. assigned to ATOCHEM North America, Inc.).

U.S. Pat. No. 4,922,007 to Kieczykowski, et al. (assigned to Merck & Co., Inc.).

U.S. Pat. No. 4,450,047 (assigned to Elf-Atochem).

U.S. Pat. No. 5,019,651 (assigned to Merck & Co., Inc.).

Venkataramani, E. S., Vaidya, F., Olsen, W. and Wittmer, S., "Create Drugs, Not Waste-Case Histories of One Company's Successes", Chemtech., p. 674, November 1992.

Wierenga, D. E. and Eaton, C. R., "The Drug Development and Approval Process", page 10 in "New Drug Approvals in 1992" presented by the Pharmaceutical Manufacturers Association, January 1992.

What is claimed is:

1. A process comprising the steps of:
   a) contacting an aqueous medium comprised of salts of omega amino $C_2$–$C_6$ alkylidene-1-hydroxy-1,1-bisphosphonic acid, methanesulfonic acid, phosphorous acid and phosphoric acid, with a calcium chloride compound in an amount of 2–10 parts by weight of calcium chloride, taken as the anhydrous salt, to 100 parts by volume of the medium;
   b) contacting said solution from step (a) with calcium oxide in a sufficient amount to cause precipitation of calcium/phosphorus containing salts formed in step (a);
   c) contacting said mixture from step (b) with hydrochloric acid to adjust the pH of the aqueous portion of the mixture to about 6–8 to cause precipitation of said calcium/phosphorus containing salts;
   d) separating said precipitated mixture of calcium/phosphorus containing salts from the aqueous medium.

2. The process of claim 1 wherein said omega amino $C_2$–$C_6$ alkylidene-1,1-bisphosphonic acid is selected from 4-amino-1-hydroxybutylidene-1,1-bisphosphonic acid, 2-amino-1-hydroxyisobutylidene-1,1-bisphosphonic acid, 3-amino-1-hydroxypropylidene-1,1-bisphosphonic acid, 5-amino-1-hydroxypentylidene-1,1-bisphosphonic acid and 6-amino-1-hydroxyhexylidene-1,1-bisphosphonic acid.

3. The process of claim 2 wherein said omega amino $C_2$–$C_6$ alkylidene-1,1-bisphosphonic acid is 4-amino-1-hydroxybutylidene-1,1-bisphosphonic acid.

4. The process of claim 1 wherein said salts of omega amino $C_2$–$C_6$ alkylidene-1-hydroxy-1,1-bisphosphoric acid, methanesulfonic acid, phosphorous and phosphoric acids are sodium salts.

5. The process of claim 1 wherein said calcium chloride compound is the hexahydrate form.

6. The process of claim 1 wherein said calcium chloride in step (a) is present in an amount of 2 to 7 weight per volume percent of mother liquor.

7. The process of claim 1 wherein the pH in step (b) is about 10–12.

8. The process of claim 1 wherein said aqueous medium is a mother liquor.

9. The process of claim 8 wherein said mother liquor is a bisphosphonation synthesis process mother liquor.

10. A process comprising the steps of:
   a) contacting an alendronate bisphosphonation process mother liquor comprised of salts of 4-amino-1-hydroxybutylidene-1,1-bisphosphonic acid, methanesulfonic acid, phosphorous acid and phosphoric acid, with a calcium chloride compound in an amount of 2–10 pans by weight of calcium chloride, taken as the anhydrous salt, to 100 pans by volume of the medium;
   b) contacting said solution from step (a) with calcium oxide in a sufficient amount to cause precipitation of calcium/phosphorus containing salts formed in step (a);
   c) contacting said mixture from step (b) with acid to adjust the pH of the aqueous portion of the mixture to about 6–8 to cause precipitation of said calcium/phosphorus containing salts;
   d) separating said precipitated mixture of calcium/phosphorus containing salts from the aqueous medium.

* * * * *